United States Patent
Dolch et al.

(10) Patent No.: US 10,724,011 B2
(45) Date of Patent: Jul. 28, 2020

(54) ALGA MODIFIED FOR INCREASED TAG PRODUCTION

(71) Applicants: FERMENTALG, Libourne (FR); COMMISSARIAT A L'ENERGIE ATOMIQUE ET AUX ENERGIES ALTERNATIVES, Paris (FR)

(72) Inventors: Lina Juana Dolch, Grenoble (FR); Camille Rak, Grenoble (FR); Fabrice Rebeille, Voreppe (FR); Juliette Jouhet, Seyssinet-Pariset (FR); Marina Leterrier, Libourne (FR); Eric Marechal, Grenoble (FR)

(73) Assignees: FERMENTALG, Libourne (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/308,226

(22) PCT Filed: Jun. 27, 2017

(86) PCT No.: PCT/EP2017/065869
§ 371 (c)(1),
(2) Date: Dec. 7, 2018

(87) PCT Pub. No.: WO2018/002059
PCT Pub. Date: Jan. 4, 2018

(65) Prior Publication Data
US 2019/0264183 A1  Aug. 29, 2019

(30) Foreign Application Priority Data
Jun. 28, 2016  (FR) ...................... 16 56007

(51) Int. Cl.
*C12N 1/12* (2006.01)
*C12N 9/10* (2006.01)
*C12P 7/64* (2006.01)

(52) U.S. Cl.
CPC ............. *C12N 9/1029* (2013.01); *C12N 1/12* (2013.01); *C12P 7/6463* (2013.01); *C12Y 203/01199* (2015.07)

(58) Field of Classification Search
CPC ..................................................... C12N 1/20
See application file for complete search history.

(56) References Cited

U.S. PATENT DOCUMENTS

| | | |
|---|---|---|
| 8,809,046 B2 | 8/2014 | Kilian et al. |
| 2012/0277418 A1 | 11/2012 | Kilian et al. |
| 2019/0264183 A1* | 8/2019 | Dolch .................. C12P 7/6463 |

FOREIGN PATENT DOCUMENTS

| | | |
|---|---|---|
| WO | WO96/21022 A2 | 7/1996 |
| WO | WO1997/037032 A2 | 10/1997 |
| WO | WO2012035262 A1 | 3/2012 |
| WO | WO2014/207043 A1 | 12/2014 |
| WO | WO2015/004403 A2 | 1/2015 |

OTHER PUBLICATIONS

Doan et al. "Enhanced intracellular lipid in *Nannochloropsis* sp. via random mutagenesis and flow cytometric cell sorting", Algal Research 1, 2012, pp. 17-21.
Anonymous "Homepage of the 22nd International Symposium on Plant Lipids", [retrieved on Jun. 26, 2016]. Retrieved from the Internet: <URL: http://web.archive.org/web/20160626005812/http://www.eurofedlipid.org/meetings/goettingen2016.
Database XP-002767332; Database accession No. W7TTK8, URL: EBI, XP002767332 [A] 1-8 sequence.
Carpinelli et al. "Chromosome Scale Genome Assembly and Transcriptome Profiling of Nannochloropsis gaditana in Nitrogen Depletion", Molecular Plant, vol. 7, No. 2, Feb. 1, 2014, pp. 323-335.
Dolch et al. "A Palmitic Acid Elongase Affects Eicosapentaenoic Acid and Plastidial Monogalactosyldiacylglycerol Levels in Nannochloropsis", Plant Physiology, vol. 173, 2017, pp. 742-759.
Simionato et al. "The Response of Nannochloropsis gaditana to Nitrogen Starvation Includes De Novo Biosynthesis of Triacylglycerols, a Decrease of Chloroplast Galactolipids, and Reorganization of the Photosynthetic Apparatus", Eukaryotic Cell, Mar. 1, 2013, vol. 12, No. 5, pp. 665-676.
Abida et al. "Membrane Glycerolipid Remodeling Triggered by Nitrogen and Phosphorus Starvation in Phaeodactylum tricornutum1", Plant Physiology, 2015, vol. 167, pp. 118-136.
Bligh et al. A rapid method of total lipid extraction and purification, Can. J. Biochem. Physiol., Aug. 1959, vol. 37, No. 8, pp. 911-917.
Cao et al. "Evaluation of putative internal reference genes for gene expression normalization in *Nannochloropsis* sp. by quantitative real-time RT-PCR", Biochemical and Biophysical Research Communications, 2012, vol. 424, pp. 118-123.
Cook et al. "Enhancing LC-PUFA production in Thalassiosira pseudonana by overexpressing the endogenous fatty acid elongase genes", J Appl Phycol, 2016, vol. 28, pp. 897-905.
Denic et al "A Molecular Caliper Mechanism for Determining Very Long-Chain Fatty Acid Length", Cell, Aug. 24, 2007, vol. 130, pp. 663-677.
Hashimoto et al. "The repertoire of desaturases and elongases reveals fatty acid variations in 56 eukaryotic genomes", Journal of Lipid Research, 2008, vol. 49, pp. 183-191.

(Continued)

*Primary Examiner* — Tekchand Saidha
(74) *Attorney, Agent, or Firm* — BCF LLP

(57) ABSTRACT

The present technology relates to a microalga that is genetically modified by inhibiting the activity of the enzyme Δ0-elongase (Δ0-ELO), which uses palmitic acid, a saturated fatty acid, as substrate and is associated with the production of monogalactosyldiacylglycerol (MGDG). The present technology also relates to a process for culturing the microalga for increased production of triacylglycerols (TAGs) and recovery of the TAGs.

8 Claims, 7 Drawing Sheets
Specification includes a Sequence Listing.

(56) References Cited

OTHER PUBLICATIONS

Jackson et al. "Identification of a consensus motif for retention of transmembrane proteins in the endoplasmic reticulum", The EMBO Journal, 1990, vol. 9, No. 10, pp. 3153-3162.
Jung et al. "The fatty acid elongase NOA is necessary for viability and has a somatic role in *Drosophila* sperm development", Journal of Cell Science, 2007, vol. 120, pp. 2924-2934.
Kihara "Very long-chain fatty acids: elongation, physiology and related disorders", J. Biochem., 2012, vol. 152, No. 5, pp. 387-395.
Kilian et al. "High-efficiency homologous recombination in the oil-producing alga *Nannochloropsis* sp.", PNAS, Dec. 27, 2011, vol. 108, No. 52, pp. 21265-21269.
Lee et al. "Fatty Acid Synthesis by Elongases in Trypanosomes", Cell, Aug. 25, 2006, vol. 126, pp. 691-699.
Ramakrishnan et al. "Apicoplast and Endoplasmic Reticulum Cooperate in Fatty Acid Biosynthesis in Apicomplexan Parasite Toxoplasma gondii", The Journal of Biological Chemistry, Feb. 10, 2012, vol. 287, No. 7, pp. 4957-4971.
Rice et al. "EMBOSS: The European Molecular Biology Open Software Suite", TIG, Jun. 2000, vol. 16, No. 6, pp. 276-277.
Sievers et al. "Fast, scalable generation of high-quality protein multiple sequence alignments using Clustal Omega", Molecular Systems Biology, 2011, vol. 7, No. 539, pp. 1-6.
Simionato et al. "The Response of Nannochloropsis gaditana to Nitrogen Starvation Includes De Novo Biosynthesis of Triacylglycerols, a Decrease of Chloroplast Galactolipids, and Reorganization of the Photosynthetic Apparatus", Eukaryotic Cell, May 2013, vol. 12, No. 5, pp. 665-676.
Tehlivets et al. "Fatty acid synthesis and elongation in yeast" Biochimica et Biophysica Acta, 2007, vol. 1771, pp. 255-270.

* cited by examiner

>Naga_100083g23.1 gene=Naga_100083g23
MHNLSEAFSKLFWGEMPKIIPYRSVPDNVPFTQLFQHYPVLSPFYTEYEKNFHASSYVNFAQNTWPALPL
ALCGIYGLMIVVGTKVMESRPKHEWKTALACWNLLLSVFSFCGMLRTVPHLLHNVTTLPFKDTICRHPAE
TYGEGACGLWVMLFIYSKVPELVDTVFIVFRKSKLQFLHWYHHITVLLFCWHSYAVTSSTGLYFVAMNYS
VHAVMYAYYYLTAIKAWPSWIPPSIITVAQISQMMVGVGICVASFYYLYTDPEHCEVKPQNVYSGALMYG
SYLYLFCDFFVRRFLRGGKPRLGEERSAVLTMTKKIKDIHDFGGWVALSPCTSCSPHMYAIEHFHHQFRG
KAEIGLKTSKHMVASIKEKKT >Naga_100162g4.1 gene=Naga_100162g4
MRPASKMTTAVCTSQWYCPPETLTATTRVYTARNTTYSFIQFWQLYPWLENFYAPFEKNFNPLPIFEFVS
GNWWVVYISLAIYMSMIIFLPMIMKKRPLKNLSTPLACWNLFLAVYSTIGAVRVVPHLLWFMSTHTFKQT
VCTAPYYINGDGATGLWVTLFTLSKVAELIDSLWICLKGRRPIFLHWYHHVSVLYFTWAAHEAAHPGMYF
IAMNYTVHSVMYTYYFLMAIKAKPKWLNPIYITFMQIAQMLVGVIISCFGFYYSSMDASCAVDPFVLKVS
AVIYASYLYLFMQFMIKRFFVKNARAGQEGKVAASAKKNI.

>Naga_100004g102.1 gene=Naga_100004g102
MARQCTKVSRYPHTLLSIMKWILREGIDFQPEGPNSRGSTFTQLFQVIPAIEPFYMEWEKKYDSSPVYEW
MKSVPWVPIAGVILYVVGIFGGQALMKNRKPFDLKWPLAYWNLALSLFSIMGMVRVVPHLIYLTATKGLG
VVACGAPEPLYGNAAVGFWVQAFILSKLAELIDTAFIVLRKKPLQFLHWYHHVTVLLFTWFCYTHENPGI
IFVAMNYSVHAIMYGYYFLMAVRVRPSWLKPQFITLMQISQMVVGVATAAFYIMKIRAGEECAVDQDLLV
ACGVMYSTYLYLFCEFAVRRFILGPKKETAPGKAGVSKMKAQ.

>Naga_100399g1.1 gene=Naga_100399g1
MQSALPAWLWRDPRPLYASSRYKTADPESPVRFVQVFQSLPWLEPFYMEWEKNFDVSSSFQVIRDNEALP
IVATILYLSFLIEGKKYIERRRREGKGPINLGLFPAFWNAFLAAFSVLGATRVVPHFLFLFTHKDFKTTV
CEAPDKAGYGDGAAGMWVMLFTVSKLFELVDTVILVLKGKDPMFLHWYHHVTVLLYTWFSYSARNPGIYF
VAMNYSVHALMYSYYFLMELRLWPKWFNPMWITMAQILQMLVGVGITVSAFFFSRDPSCALVRGLIPWCA
AMYATYLYFFVLFFLERFFPAFKPAAPGAARGLSGGKAGRTGGGGGGEGGGRCRRRGKGGGDSGPRRGK >Naga_100162g5.1 gene=Naga_100162g5
MSEALANLSHPCTSSLYCPPSSLVPVTRELAGHTYTFLQFWQLFPWSEPFYTRLEKEFDVRPWYLFVHAN
GWLPVVSIILYAAMVLLLPPITSKRPVKCDTALAYWNLLLAAFSILGALRIVPHLLWFLTTHSFKETVCT
PPERMNGDGASGLWCLLFTLSKLVELVDTMFVCLKGRKPIFLHWYHHVTVLSFTWAAYSARHPGMYFIAM
NYTVHAVMYSYYFLMAIKAKPKWLNPIYITFLQIFQMVAGVIITVYGFIYARDPSTCGVVPSVLYFQSVI
YGSYLYLFLEFLVKRFFCPPQSVPPASRPVGKEDQGREEGWKTAMTNGAGTHFKKAQ.

>Naga_100017g49.1 gene=Naga_100017g49
MSWFLDPAPLYETSQYITRDPVKPVRFVQVFQAIPALEPFYTEWEKHFDVSAPFRAIRDSKWVPIMAVIL
YLSFLVEGKKYIERRKKEGKGPVNLGYFPALWNGFLALFSIAGALRVVPHFLFLFTHKDFKETVCEAPDA
AGYGDGAAGLWVMLFTVSKVFELMDTVILVLKGKDPMFLHWYHHVTVLLYTWFSYSARNPGLYFIAMNYT
VHAVMYSYYFLMELRLWPKWLSPVFITLMQISQMLVGVGVTAAAYSYQADPSCAVVRDLIPWCAAMYATY
LYFFVEFFVERFLAASTKRTPVSKLASKDIGAAPSNEGRDKKKT

Fig. 2

MHNLSEAFSKLFWGEMPKIIPYRSVPDNVPFTQLFQHYPVLSPFYTEYEK

NFHASSYVNFAQNTWPALPLALCGIYGLMIVVGTKVMESRPKHEWKTALA
　　　　　　　　　　TM1

TM2
CWNLLLSVFSFCGMLRTVPHLLHNVTTLPFKDTICRHPAETYGEGACGLW
　　　　TM3　　　　　　　　　　　　　TM4
VMLFIYSKVPELVDTVFIVFRKSKLQFLHWYHHITVLLFCWHSYAVTSST
　　TM5　　　　　　　　　　　　　　　　　　　TM6
GLYFVAMNYSVHAVMYAYYYLTAIKAWPSWIPPSIITVAQISQMMVGVGI
　　　　　　　　　　　　　　TM7
CVASFYYLTDPEHCEVKPQNVYSGALMYGSYLYLFCDFFVRRFLRGGKP

RLGEERSAVLTMTKKIKDIHDFGGWVALSPCTSCSPHMYAIEHFHHQFRG

KAEIGLKTSKHMVASIKEKKT

Fig. 4

```
Naga_100083g2    66  PALPLALCGIYGLMIVVGTKVMESRPKHEWKTALACWNLLLSVFSFCGML   115
                     |.:|:..|.:|||:|.|.....:|.....|:||.|||.|::||..|||
Phaeodactylum     5  PLVPIGACLLYGLLMVAGQAYFRTREPLRARTSLAAWNLFLALFSLVGML    54

Naga_100083g2   116  RTVPHLLHNVTTLPFKDTICRHPAETYGEGACGLWVMLFIYSKVPELVDT   165
                     ||.|.|:||:.||..::.:|.:|..|||.|:.||||.|||.||.|||:||
Phaeodactylum    55  RTFPQLVHNLATLTLRENLCANPQATYGSGSTGLWVQLFILSKFPELIDT   104

Naga_100083g2   166  VFIVFRKSKLQFLHWYHHITVLLFCWHSYAVTSSTGLYFVAMNYSVHAVM   215
                     |||:..|.||.||||||||||||.|:||||.|...|..|::||.|||:||.|
Phaeodactylum   105  VFIIVNKKKLIFLHWYHHITVLLYCWHSYVTKSPPGIFFVVMNYTVHASM   154

Naga_100083g2   216  YAYYYLTAIKAWPSWIPPSIITVAQISQMMVGVGICVASFYYLYTDPEH-   264
                     |.||:|.||:|.|.|:.|.|.|:|...|||||||:||||.|:|||.|||
Phaeodactylum   155  YGYYFLMAIRARPRWLNPMIVTTMQISQMVVGVAVTLLGFYYSARAADHQ   204

Naga_100083g2   265  -CEVKPQNVYSGALMYGSYLYLFCDFFVRRFLRGGKP              300
                      |.:|.:|...:.:||||||:||..|||.|.::....|
Phaeodactylum   205  SCRIKRENNTAAFVMYGSYLFLFLQFFVGRYVGTQSP              241
```

Fig. 5

```
Naga_100083g2   20  IPYRSVPDN---VPFTQLFQHYPVLSPFYTEYEKNFHASSYVNFAQNTW-    65
                    ||...||..|  |.:.:....:|:|...|..:|:    .|....|..||
Thalassiosira    8  IPKECVGTNGLGVHYAEFSCLHPLLGATYLPFER-----FYDPVATLTWM    52

Naga_100083g2   66  ---PALPLALCGIYGLMIVVGTKVMESRPKHEWKTALACWNLLLSVFSFC   112
                       |.:|:..|..|.:|||:|...|:.|...|:..||.|||.||:||:.
Thalassiosira   53  QDRPMIPIIACVAYVVLIVLGRAYMKDRPAWSWRRILAVWNLSLSLFSWI   102

Naga_100083g2  113  GMLRTVPHLLHNVTTLPFKDTICRHPAETYGEGACGLWVMLFIYSKVPEL   162
                    |.:||.|.|.:|:|||...:|.:|..||..||.|:.||||.|||.||.|||
Thalassiosira  103  GAIRTAPQLYYNLTTYSLRDNLCDDPAALYGSGTGLWVQLFILSKFPEL    152

Naga_100083g2  163  VDTVFIVFRKSKLQFLHWYHHITVLLFCWHSYAVTSSTGLYFVAMNYSVH   212
                    :||.|||..|..|.|||||||||||||||:|||||..||.:||:||.||||||
Thalassiosira  153  LDTFFIVIHKKPLIFLHWYHHITVLLYCWHSYVTTSPSGLFFVVMNYSVH   202

Naga_100083g2  213  AVMYAYYYLTAIKAWPSWIPPSIITVAQISQMMVGVGICVASFYYLYTDP   262
                    ||||.||:|.|:|..|.|..|..:|.|:|||.:||||:.:.:|||  |::|
Thalassiosira  203  AVMYGYYFLMAVKFRPKWFNPMFVTFMQLSQMFIGVGVTIVAFYY-YSNP   251

Naga_100083g2  263  ---EHCEVKPQNVYSGALMYGSYLYLFCDFFVRRFLR         296
                    :.|.::.:|..:..:|||||.|||..|||.|:.:
Thalassiosira  252  ILGKTCHIRKENNVAAFVMYGSYFYLFAQFFVARYYK         288
```

Fig. 6

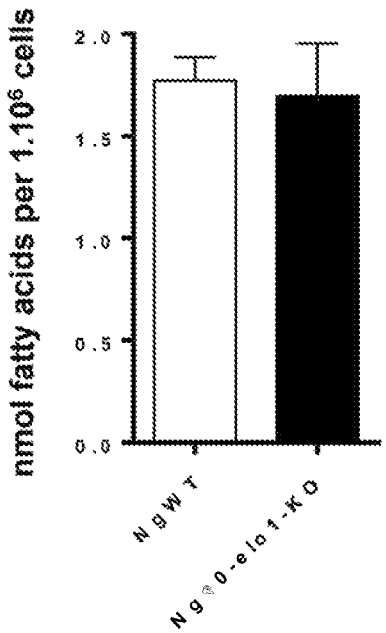

Fig. 7A

SEQUENCE LISTING

```
<160> NUMBER OF SEQ ID NOS: 24

<210> SEQ ID NO 1
<211> LENGTH: 371
<212> TYPE: PRT
<213> ORGANISM: Nannochloropsis gaditana
<220> FEATURE:
<223> OTHER INFORMATION: Naga_100083g23

<400> SEQUENCE: 1

Met His Asn Leu Ser Glu Ala Phe Ser Lys Leu Phe Trp Gly Glu Met
1               5                   10                  15

Pro Lys Ile Ile Pro Tyr Arg Ser Val Pro Asp Asn Val Pro Phe Thr
            20                  25                  30

Gln Leu Phe Gln His Tyr Pro Val Leu Ser Pro Phe Tyr Thr Glu Tyr
        35                  40                  45

Glu Lys Asn Phe His Ala Ser Ser Tyr Val Asn Phe Ala Gln Asn Thr
    50                  55                  60

Trp Pro Ala Leu Pro Leu Ala Leu Cys Gly Ile Tyr Gly Leu Met Ile
65                  70                  75                  80

Val Val Gly Thr Lys Val Met Glu Ser Arg Pro Lys His Glu Trp Lys
                85                  90                  95

Thr Ala Leu Ala Cys Trp Asn Leu Leu Leu Ser Val Phe Ser Phe Cys
            100                 105                 110

Gly Met Leu Arg Thr Val Pro His Leu Leu His Asn Val Thr Thr Leu
        115                 120                 125

Pro Phe Lys Asp Thr Ile Cys Arg His Pro Ala Glu Thr Tyr Gly Glu
    130                 135                 140

Gly Ala Cys Gly Leu Trp Val Met Leu Phe Ile Tyr Ser Lys Val Pro
145                 150                 155                 160

Glu Leu Val Asp Thr Val Phe Ile Val Phe Arg Lys Ser Lys Leu Gln
                165                 170                 175

Phe Leu His Trp Tyr His His Ile Thr Val Leu Leu Phe Cys Trp His
            180                 185                 190

Ser Tyr Ala Val Thr Ser Ser Thr Gly Leu Tyr Phe Val Ala Met Asn
        195                 200                 205

Tyr Ser Val His Ala Val Met Tyr Ala Tyr Tyr Leu Thr Ala Ile
    210                 215                 220

Lys Ala Trp Pro Ser Trp Ile Pro Pro Ser Ile Ile Thr Val Ala Gln
225                 230                 235                 240

Ile Ser Gln Met Met Val Gly Val Gly Ile Cys Val Ala Ser Phe Tyr
                245                 250                 255

Tyr Leu Tyr Thr Asp Pro Glu His Cys Glu Val Lys Pro Gln Asn Val
            260                 265                 270

Tyr Ser Gly Ala Leu Met Tyr Gly Ser Tyr Leu Tyr Leu Phe Cys Asp
        275                 280                 285
```

Phe Phe Val Arg Arg Phe Leu Arg Gly Gly Lys Pro Arg Leu Gly Glu
            290                 295                 300
Glu Arg Ser Ala Val Leu Thr Met Thr Lys Lys Ile Lys Asp Ile His
305                 310                 315                 320
Asp Phe Gly Gly Trp Val Ala Leu Ser Pro Cys Thr Ser Cys Ser Pro
                325                 330                 335
His Met Tyr Ala Ile Glu His Phe His Gln Phe Arg Gly Lys Ala
                340                 345                 350
Glu Ile Gly Leu Lys Thr Ser Lys His Met Val Ala Ser Ile Lys Glu
            355                 360                 365
Lys Lys Thr
    370

<210> SEQ ID NO 2
<211> LENGTH: 320
<212> TYPE: PRT
<213> ORGANISM: Nannochloropsis gaditana
<220> FEATURE:
<223> OTHER INFORMATION: Naga_100162g4

<400> SEQUENCE: 2

Met Arg Pro Ala Ser Lys Met Thr Thr Ala Val Cys Thr Ser Gln Trp
1               5                   10                  15
Tyr Cys Pro Pro Glu Thr Leu Thr Ala Thr Arg Val Tyr Thr Ala
                20                  25                  30
Arg Asn Thr Thr Tyr Ser Phe Ile Gln Phe Trp Gln Leu Tyr Pro Trp
                35                  40                  45
Leu Glu Asn Phe Tyr Ala Pro Phe Glu Lys Asn Phe Asn Pro Leu Pro
    50                  55                  60
Ile Phe Glu Phe Val Ser Gly Asn Trp Trp Val Val Tyr Ile Ser Leu
65                  70                  75                  80
Ala Ile Tyr Met Ser Met Ile Ile Phe Leu Pro Met Ile Met Lys Lys
                85                  90                  95
Arg Pro Leu Lys Asn Leu Ser Thr Pro Leu Ala Cys Trp Asn Leu Phe
                100                 105                 110
Leu Ala Val Tyr Ser Thr Ile Gly Ala Val Arg Val Pro His Leu
                115                 120                 125
Leu Trp Phe Met Ser Thr His Thr Phe Lys Gln Thr Val Cys Thr Ala
130                 135                 140
Pro Tyr Tyr Ile Asn Gly Asp Gly Ala Thr Gly Leu Trp Val Thr Leu
145                 150                 155                 160
Phe Thr Leu Ser Lys Val Ala Glu Leu Ile Asp Ser Leu Trp Ile Cys
                165                 170                 175
Leu Lys Gly Arg Arg Pro Ile Phe Leu His Trp Tyr His Val Ser
                180                 185                 190
Val Leu Tyr Phe Thr Trp Ala Ala His Glu Ala Ala His Pro Gly Met
    195                 200                 205
Tyr Phe Ile Ala Met Asn Tyr Thr Val His Ser Val Met Tyr Thr Tyr
210                 215                 220
Tyr Phe Leu Met Ala Ile Lys Ala Lys Pro Lys Trp Leu Asn Pro Ile
225                 230                 235                 240
Tyr Ile Thr Phe Met Gln Ile Ala Gln Met Leu Val Gly Val Ile Ile
                245                 250                 255
Ser Cys Phe Gly Phe Tyr Tyr Ser Met Asp Ala Ser Cys Ala Val
                260                 265                 270

```
Asp Pro Phe Val Leu Lys Val Ser Ala Val Ile Tyr Ala Ser Tyr Leu
            275                 280                 285

Tyr Leu Phe Met Gln Phe Met Ile Lys Arg Phe Val Lys Asn Ala
290                 295                 300

Arg Ala Gly Gln Glu Gly Lys Val Ala Ala Ser Ala Lys Lys Asn Ile
305                 310                 315                 320

<210> SEQ ID NO 3
<211> LENGTH: 322
<212> TYPE: PRT
<213> ORGANISM: Nannochloropsis gaditana
<220> FEATURE:
<223> OTHER INFORMATION: Naga_100004g102

<400> SEQUENCE: 3

Met Ala Arg Gln Cys Thr Lys Val Ser Arg Tyr Pro His Thr Leu Leu
1               5                   10                  15

Ser Ile Met Lys Trp Ile Leu Arg Glu Gly Ile Asp Phe Gln Pro Glu
            20                  25                  30

Gly Pro Asn Ser Arg Gly Ser Thr Phe Thr Gln Leu Phe Gln Val Ile
        35                  40                  45

Pro Ala Ile Glu Pro Phe Tyr Met Glu Trp Lys Lys Tyr Asp Ser
50                  55                  60

Ser Pro Val Tyr Glu Trp Met Lys Ser Val Pro Trp Val Pro Ile Ala
65                  70                  75                  80

Gly Val Ile Leu Tyr Val Val Gly Ile Phe Gly Gly Gln Ala Leu Met
                85                  90                  95

Lys Asn Arg Lys Pro Phe Asp Leu Lys Trp Pro Leu Ala Tyr Trp Asn
            100                 105                 110

Leu Ala Leu Ser Leu Phe Ser Ile Met Gly Met Val Arg Val Val Pro
        115                 120                 125

His Leu Ile Tyr Leu Thr Ala Thr Lys Gly Leu Gly Val Val Ala Cys
    130                 135                 140

Gly Ala Pro Glu Pro Leu Tyr Gly Asn Ala Ala Val Gly Phe Trp Val
145                 150                 155                 160

Gln Ala Phe Ile Leu Ser Lys Leu Ala Glu Leu Ile Asp Thr Ala Phe
                165                 170                 175

Ile Val Leu Arg Lys Lys Pro Leu Gln Phe Leu His Trp Tyr His His
            180                 185                 190

Val Thr Val Leu Leu Phe Thr Trp Phe Cys Tyr Thr His Glu Asn Pro
        195                 200                 205

Gly Ile Ile Phe Val Ala Met Asn Tyr Ser Val His Ala Ile Met Tyr
    210                 215                 220

Gly Tyr Tyr Phe Leu Met Ala Val Arg Val Arg Pro Ser Trp Leu Lys
225                 230                 235                 240

Pro Gln Phe Ile Thr Leu Met Gln Ile Ser Gln Met Val Val Gly Val
                245                 250                 255

Ala Thr Ala Ala Phe Tyr Ile Met Lys Ile Arg Ala Gly Glu Glu Cys
            260                 265                 270

Ala Val Asp Gln Asp Leu Leu Val Ala Cys Gly Val Met Tyr Ser Thr
        275                 280                 285

Tyr Leu Tyr Leu Phe Cys Glu Phe Ala Val Arg Arg Phe Ile Leu Gly
    290                 295                 300

Pro Lys Lys Glu Thr Ala Pro Gly Lys Ala Gly Val Ser Lys Met Lys
305                 310                 315                 320
```

Ala Gln

<210> SEQ ID NO 4
<211> LENGTH: 350
<212> TYPE: PRT
<213> ORGANISM: Nannochloropsis gaditana
<220> FEATURE:
<223> OTHER INFORMATION: Naga_100004g102

<400> SEQUENCE: 4

```
Met Gln Ser Ala Leu Pro Ala Trp Leu Trp Arg Asp Pro Arg Pro Leu
1               5                   10                  15

Tyr Ala Ser Ser Arg Tyr Lys Thr Ala Asp Pro Glu Ser Pro Val Arg
            20                  25                  30

Phe Val Gln Val Phe Gln Ser Leu Pro Trp Leu Glu Pro Phe Tyr Met
        35                  40                  45

Glu Trp Glu Lys Asn Phe Asp Val Ser Ser Phe Gln Val Ile Arg
50                  55                  60

Asp Asn Glu Ala Leu Pro Ile Val Ala Thr Ile Leu Tyr Leu Ser Phe
65                  70                  75                  80

Leu Ile Glu Gly Lys Lys Tyr Ile Glu Arg Arg Arg Glu Gly Lys
                85                  90                  95

Gly Pro Ile Asn Leu Gly Leu Phe Pro Ala Phe Trp Asn Ala Phe Leu
            100                 105                 110

Ala Ala Phe Ser Val Leu Gly Ala Thr Arg Val Val Pro His Phe Leu
        115                 120                 125

Phe Leu Phe Thr His Lys Asp Phe Lys Thr Thr Val Cys Glu Ala Pro
    130                 135                 140

Asp Lys Ala Gly Tyr Gly Asp Gly Ala Ala Gly Met Trp Val Met Leu
145                 150                 155                 160

Phe Thr Val Ser Lys Leu Phe Glu Leu Val Asp Thr Val Ile Leu Val
                165                 170                 175

Leu Lys Gly Lys Asp Pro Met Phe Leu His Trp Tyr His His Val Thr
            180                 185                 190

Val Leu Leu Tyr Thr Trp Phe Ser Tyr Ser Ala Arg Asn Pro Gly Ile
        195                 200                 205

Tyr Phe Val Ala Met Asn Tyr Ser Val His Ala Leu Met Tyr Ser Tyr
    210                 215                 220

Tyr Phe Leu Met Glu Leu Arg Leu Trp Pro Lys Trp Phe Asn Pro Met
225                 230                 235                 240

Trp Ile Thr Met Ala Gln Ile Leu Gln Met Leu Val Gly Val Gly Ile
                245                 250                 255

Thr Val Ser Ala Phe Phe Ser Arg Asp Pro Ser Cys Ala Leu Val
            260                 265                 270

Arg Gly Leu Ile Pro Trp Cys Ala Ala Met Tyr Ala Thr Tyr Leu Tyr
        275                 280                 285

Phe Phe Val Leu Phe Leu Glu Arg Phe Pro Ala Phe Lys Pro
    290                 295                 300

Ala Ala Pro Gly Ala Ala Arg Gly Leu Ser Gly Gly Lys Ala Gly Arg
305                 310                 315                 320

Thr Gly Gly Gly Gly Gly Gly Glu Gly Gly Arg Cys Arg Arg
                325                 330                 335

Arg Gly Lys Gly Gly Gly Asp Ser Gly Pro Arg Arg Gly Lys
            340                 345                 350
```

```
<210> SEQ ID NO 5
<211> LENGTH: 337
<212> TYPE: PRT
<213> ORGANISM: Nannochloropsis gaditana
<220> FEATURE:
<223> OTHER INFORMATION: Naga_100162g5

<400> SEQUENCE: 5
```

Met Ser Glu Ala Leu Ala Asn Leu Ser His Pro Cys Thr Ser Ser Leu
1               5                   10                  15

Tyr Cys Pro Pro Ser Ser Leu Val Pro Val Thr Arg Glu Leu Ala Gly
            20                  25                  30

His Thr Tyr Thr Phe Leu Gln Phe Trp Gln Leu Phe Pro Trp Ser Glu
        35                  40                  45

Pro Phe Tyr Thr Arg Leu Glu Lys Glu Phe Asp Val Arg Pro Trp Tyr
    50                  55                  60

Leu Phe Val His Ala Asn Gly Trp Leu Pro Val Val Ser Ile Ile Leu
65                  70                  75                  80

Tyr Ala Ala Met Val Leu Leu Leu Pro Pro Ile Thr Ser Lys Arg Pro
                85                  90                  95

Val Lys Cys Asp Thr Ala Leu Ala Tyr Trp Asn Leu Leu Leu Ala Ala
            100                 105                 110

Phe Ser Ile Leu Gly Ala Leu Arg Ile Val Pro His Leu Leu Trp Phe
        115                 120                 125

Leu Thr Thr His Ser Phe Lys Glu Thr Val Cys Thr Pro Pro Glu Arg
    130                 135                 140

Met Asn Gly Asp Gly Ala Ser Gly Leu Trp Cys Leu Leu Phe Thr Leu
145                 150                 155                 160

Ser Lys Leu Val Glu Leu Val Asp Thr Met Phe Val Cys Leu Lys Gly
                165                 170                 175

Arg Lys Pro Ile Phe Leu His Trp Tyr His Val Thr Val Leu Ser
            180                 185                 190

Phe Thr Trp Ala Ala Tyr Ser Ala Arg His Pro Gly Met Tyr Phe Ile
        195                 200                 205

Ala Met Asn Tyr Thr Val His Ala Val Met Tyr Ser Tyr Tyr Phe Leu
    210                 215                 220

Met Ala Ile Lys Ala Lys Pro Lys Trp Leu Asn Pro Ile Tyr Ile Thr
225                 230                 235                 240

Phe Leu Gln Ile Phe Gln Met Val Ala Gly Val Ile Ile Thr Val Tyr
                245                 250                 255

Gly Phe Ile Tyr Ala Arg Asp Pro Ser Thr Cys Gly Val Val Pro Ser
            260                 265                 270

Val Leu Tyr Phe Gln Ser Val Ile Tyr Gly Ser Tyr Leu Tyr Leu Phe
        275                 280                 285

Leu Glu Phe Leu Val Lys Arg Phe Cys Pro Pro Gln Ser Val Pro
    290                 295                 300

Pro Ala Ser Arg Pro Val Gly Lys Glu Asp Gln Gly Arg Glu Glu Gly
305                 310                 315                 320

Trp Lys Thr Ala Met Thr Asn Gly Ala Gly Thr His Phe Lys Lys Ala
                325                 330                 335

Gln

```
<210> SEQ ID NO 6
<211> LENGTH: 324
<212> TYPE: PRT
<213> ORGANISM: Nannochloropsis gaditana
```

<220> FEATURE:
<223> OTHER INFORMATION: Naga_100017g49

<400> SEQUENCE: 6

Met Ser Trp Phe Leu Asp Pro Ala Pro Leu Tyr Glu Thr Ser Gln Tyr
1               5                   10                  15

Ile Thr Arg Asp Pro Val Lys Pro Val Arg Phe Val Gln Val Phe Gln
            20                  25                  30

Ala Ile Pro Ala Leu Glu Pro Phe Tyr Thr Glu Trp Glu Lys His Phe
        35                  40                  45

Asp Val Ser Ala Pro Phe Arg Ala Ile Arg Asp Ser Lys Trp Val Pro
    50                  55                  60

Ile Met Ala Val Ile Leu Tyr Leu Ser Phe Leu Val Glu Gly Lys Lys
65                  70                  75                  80

Tyr Ile Glu Arg Arg Lys Lys Glu Gly Lys Gly Pro Val Asn Leu Gly
                85                  90                  95

Tyr Phe Pro Ala Leu Trp Asn Gly Phe Leu Ala Leu Phe Ser Ile Ala
            100                 105                 110

Gly Ala Leu Arg Val Val Pro His Phe Leu Phe Leu Phe Thr His Lys
        115                 120                 125

Asp Phe Lys Glu Thr Val Cys Glu Ala Pro Asp Ala Ala Gly Tyr Gly
    130                 135                 140

Asp Gly Ala Ala Gly Leu Trp Val Met Leu Phe Thr Val Ser Lys Val
145                 150                 155                 160

Phe Glu Leu Met Asp Thr Val Ile Leu Val Leu Lys Gly Lys Asp Pro
                165                 170                 175

Met Phe Leu His Trp Tyr His His Val Thr Val Leu Leu Tyr Thr Trp
            180                 185                 190

Phe Ser Tyr Ser Ala Arg Asn Pro Gly Leu Tyr Phe Ile Ala Met Asn
        195                 200                 205

Tyr Thr Val His Ala Val Met Tyr Ser Tyr Tyr Phe Leu Met Glu Leu
    210                 215                 220

Arg Leu Trp Pro Lys Trp Leu Ser Pro Val Phe Ile Thr Leu Met Gln
225                 230                 235                 240

Ile Ser Gln Met Leu Val Gly Val Gly Val Thr Ala Ala Ala Tyr Ser
                245                 250                 255

Tyr Gln Ala Asp Pro Ser Cys Ala Val Val Arg Asp Leu Ile Pro Trp
            260                 265                 270

Cys Ala Ala Met Tyr Ala Thr Tyr Leu Tyr Phe Phe Val Glu Phe Phe
        275                 280                 285

Val Glu Arg Phe Leu Ala Ala Ser Thr Lys Arg Thr Pro Val Ser Lys
    290                 295                 300

Leu Ala Ser Lys Asp Ile Gly Ala Ala Pro Ser Asn Glu Gly Arg Asp
305                 310                 315                 320

Lys Lys Lys Thr

<210> SEQ ID NO 7
<211> LENGTH: 248
<212> TYPE: PRT
<213> ORGANISM: Phaedactylum
<220> FEATURE:
<223> OTHER INFORMATION: delta-elongase

<400> SEQUENCE: 7

Met Glu Ala His Pro Leu Val Pro Ile Gly Ala Cys Leu Leu Tyr Gly
1               5                   10                  15

Leu Leu Met Val Ala Gly Gln Ala Tyr Phe Arg Thr Arg Glu Pro Leu
            20                  25                  30

Arg Ala Arg Thr Ser Leu Ala Ala Trp Asn Leu Phe Leu Ala Leu Phe
        35                  40                  45

Ser Leu Val Gly Met Leu Arg Thr Phe Pro Gln Leu Val His Asn Leu
    50                  55                  60

Ala Thr Leu Thr Leu Arg Glu Asn Leu Cys Ala Asn Pro Gln Ala Thr
65                  70                  75                  80

Tyr Gly Ser Gly Ser Thr Gly Leu Trp Val Gln Leu Phe Ile Leu Ser
                85                  90                  95

Lys Phe Pro Glu Leu Ile Asp Thr Val Phe Ile Val Asn Lys Lys
            100                 105                 110

Lys Leu Ile Phe Leu His Trp Tyr His His Ile Thr Val Leu Leu Tyr
        115                 120                 125

Cys Trp His Ser Tyr Val Thr Lys Ser Pro Pro Gly Ile Phe Phe Val
    130                 135                 140

Val Met Asn Tyr Thr Val His Ala Ser Met Tyr Gly Tyr Tyr Phe Leu
145                 150                 155                 160

Met Ala Ile Arg Ala Arg Pro Arg Trp Leu Asn Pro Met Ile Val Thr
                165                 170                 175

Thr Met Gln Ile Ser Gln Met Val Val Gly Val Ala Val Thr Leu Leu
            180                 185                 190

Gly Phe Tyr Tyr Ser Ala Arg Ala Ala Asp His Gln Ser Cys Arg Ile
        195                 200                 205

Lys Arg Glu Asn Asn Thr Ala Ala Phe Val Met Tyr Gly Ser Tyr Leu
    210                 215                 220

Phe Leu Phe Leu Gln Phe Phe Val Gly Arg Tyr Val Gly Thr Gln Ser
225                 230                 235                 240

Pro Val Ala Ser Lys Lys Thr Ala
                245

<210> SEQ ID NO 8
<211> LENGTH: 301
<212> TYPE: PRT
<213> ORGANISM: Thalassiosira
<220> FEATURE:
<223> OTHER INFORMATION: delta-elongase

<400> SEQUENCE: 8

Met Ser Gln Phe Leu Thr Ser Ile Pro Lys Glu Cys Val Gly Thr Asn
1               5                   10                  15

Gly Leu Gly Val His Tyr Ala Glu Phe Ser Cys Leu His Pro Leu Leu
            20                  25                  30

Gly Ala Thr Tyr Leu Pro Phe Glu Arg Phe Tyr Asp Pro Val Ala Thr
        35                  40                  45

Leu Thr Trp Met Gln Asp Arg Pro Met Ile Pro Ile Ile Ala Cys Val
    50                  55                  60

Ala Tyr Val Val Leu Ile Val Leu Gly Arg Ala Tyr Met Lys Asp Arg
65                  70                  75                  80

Pro Ala Trp Ser Trp Arg Arg Ile Leu Ala Val Trp Asn Leu Ser Leu
                85                  90                  95

Ser Leu Phe Ser Trp Ile Gly Ala Ile Arg Thr Ala Pro Gln Leu Tyr
            100                 105                 110

Tyr Asn Leu Thr Thr Tyr Ser Leu Arg Asp Asn Leu Cys Asp Asp Pro
        115                 120                 125

Ala Ala Leu Tyr Gly Ser Gly Ser Thr Gly Leu Trp Val Gln Leu Phe
            130                 135                 140

Ile Leu Ser Lys Phe Pro Glu Leu Leu Asp Thr Phe Phe Ile Val Ile
145                 150                 155                 160

His Lys Lys Pro Leu Ile Phe Leu His Trp Tyr His His Ile Thr Val
                165                 170                 175

Leu Leu Tyr Cys Trp His Ser Tyr Val Thr Thr Ser Pro Ser Gly Leu
            180                 185                 190

Phe Phe Val Val Met Asn Tyr Ser Val His Ala Val Met Tyr Gly Tyr
        195                 200                 205

Tyr Phe Leu Met Ala Val Lys Phe Arg Pro Lys Trp Phe Asn Pro Met
    210                 215                 220

Phe Val Thr Phe Met Gln Leu Ser Gln Met Phe Ile Gly Val Gly Val
225                 230                 235                 240

Thr Ile Val Ala Phe Tyr Tyr Ser Asn Pro Ile Leu Gly Lys Thr
                245                 250                 255

Cys His Ile Arg Lys Glu Asn Asn Val Ala Ala Phe Val Met Tyr Gly
            260                 265                 270

Ser Tyr Phe Tyr Leu Phe Ala Gln Phe Phe Val Ala Arg Tyr Tyr Lys
        275                 280                 285

Val Lys Val Lys Gly Asp Ala Lys Lys Lys Val Val
    290                 295                 300

<210> SEQ ID NO 9
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 9
gttgggaata atgcgggacc                                              20

<210> SEQ ID NO 10
<211> LENGTH: 20
<212> TYPE: PRT
<213> ORGANISM: Artificial sequence
<220> FEATURE:
<223> OTHER INFORMATION: synthetic oligonucleotide

<400> SEQUENCE: 10

Cys Cys Gly Cys Thr Thr Thr Gly Gly Thr Thr Thr Cys Ala Cys Ala
1               5                   10                  15

Gly Thr Cys Ala
            20

<210> SEQ ID NO 11
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 11
acgatgggta tgttgcttgc                                              20

<210> SEQ ID NO 12
<211> LENGTH: 20
<212> TYPE: DNA
<213> ORGANISM: Artificial sequence

```
<220> FEATURE:
<223> OTHER INFORMATION: synthetic oligonucleotide

<400> SEQUENCE: 12
tgtacagggc ggatttcact                                              20

<210> SEQ ID NO 13
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 13
gaggaatgtg tgtggttggg                                              20

<210> SEQ ID NO 14
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 14
gccgtattgt tggagtggac                                              20

<210> SEQ ID NO 15
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 15
gacacttctc tgcctttgcc                                              20

<210> SEQ ID NO 16
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 16
atggtggtac cagtggagga                                              20

<210> SEQ ID NO 17
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 17
gtgggcacca aggttatgga                                              20

<210> SEQ ID NO 18
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 18
gaaggaggtg tggtacggtg                                              20
```

<210> SEQ ID NO 19
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 19
aagtggtacc tttgctccgt                                                    20

<210> SEQ ID NO 20
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 20
aaggtagccg agtagccaaa                                                    20

<210> SEQ ID NO 21
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 21
ttgagcatac cgacgtgact                                                    20

<210> SEQ ID NO 22
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 22
gcgatgagcc tgttcagatt                                                    20

<210> SEQ ID NO 23
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 23
tgtgccaaaa tcatacagca gg                                                 22

<210> SEQ ID NO 24
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 24
cgaagtcgtc ctccacgaag                                                    20

ALGA MODIFIED FOR INCREASED TAG PRODUCTION

CROSS-REFERENCE TO RELATED APPLICATIONS

The present Application is a United States National Stage Patent Application of International Application No. PCT/EP2017/065869, filed on Jun. 27, 2017 which claims priority from French Patent Application No. 1656007, filed Jun. 28, 2016, the content of which is herein incorporated in its entirety by reference.

FIELD OF THE INVENTION

The present invention concerns a microalga that is genetically modified by inhibiting the activity of the enzyme Δ0-elongase (Δ0-ELO), which uses palmitic acid, a saturated fatty acid, as substrate and is associated with the production of monogalactosyldiacylglycerol (MGDG). It also concerns a process for culturing said microalga for increased production of triacylglycerols (TAGs) and recovery of said TAGs.

STATE OF THE ART

The synthesis pathways for long-chain polyunsaturated fatty acids have been studied and are known to the skilled person for plants and microalgae. They generally consist in the synthesis of oleic acid, a C18 fatty acid with a double bond (18:1), and of linoleic acid (18:2), in the form of thioesters with coenzyme A, then in a series of elongations with the creation of unsaturations by the alternating action of elongases and desaturases. Several elongases that are active on desaturated fatty acids (containing double bonds) have been described in the state of the art (Cook and Hildebrand, 2015; Jung et al., 2007; Kihara, 2012; Lee et al., 2006; Ramakrishnan et al., 2012; Tehlivets et al., 2007). *Nannochloropsis* elongases, which are active on desaturated fatty acids, are also described in U.S. Pat. No. 8,809,046.

The skilled person also knows how to act on the expression of the enzymes involved in (poly)unsaturated fatty acid biosynthesis in plants or microalgae to modulate this biosynthesis. Particular mention may be made of patent application WO 96/21022 for the synthesis of gamma-linolenic acid.

Application WO 2014/207043 describes the preparation of microalgae genetically modified by knocking-out (KO) certain genes. The use of a TALE nuclease for targeted gene mutagenesis in microalgae is described. Several examples of gene targeting are given, notably the targeting of a Δ6-elongase (Δ6-ELO), active on a fatty acid with a double bond at position Δ6.

In that application, the authors claim to obtain an increase in TAGs by inhibiting the expression of a Δ6-ELO but remain silent on their ability to grow the resulting clones over time. The increase in TAGs asserted in application WO 2014/207043 is also accompanied by an inhibition of cell growth.

However, for the industrial use of microalgae to produce unsaturated fatty acids and TAGs, it is also necessary to have strains capable of ensuring good cell growth to produce the TAG-rich biomass. The skilled person therefore seeks to have genetically modified strains that make it possible to increase TAG production without affecting their growth.

SUMMARY OF THE INVENTION

The present invention concerns genetically modified microalgae in which the elongase (Δ0-ELO) activity is inhibited.

The invention concerns in particular genetically modified microalgae selected from the microalgae containing photosynthetic organelles, notably the genera *Crypthecodinium, Chlorella, Cyclotella, Euglena, Haematococcus, Isochrysis, Monodus, Nanochloris, Nannochloropsis, Nitzschia, Odontella, Phaeodactylum, Scenedesmus, Tetraselmis*, and *Thalassiosira*.

Preferably, the invention concerns microalgae for which the Δ0-ELO activity is multigenic, and more preferentially when only the Δ0-ELO activity associated with MGDG production is inhibited.

The invention also concerns a process for producing a TAG-enriched biomass which comprises culturing genetically modified microalgae according to the invention on a culture medium suitable for promoting the growth and multiplication of microorganism cells. The invention also concerns a TAG production process that comprises obtaining the TAG-enriched biomass and isolating the TAGs thus produced.

DESCRIPTION OF THE FIGURES

FIG. 2 shows the sequences of six *Nannochloropsis gaditana* saturated fatty acid Δ0-ELO: Naga_100083g23 (SEQ ID NO 1), Naga_100162g4 (SEQ ID NO 2), Naga_100004g102 (SEQ ID NO 3), Naga_100399g1 (SEQ ID NO 4), Naga_100162g5 (SEQ ID NO 5) and Naga_100017g49 (SEQ ID NO 6).

FIG. 4 shows the amino acid sequence of NgΔ0-ELO1 (Naga_100083g23). The characteristic elongase motifs were identified according to (Denic and Weissman, 2007) and (Hashimoto et al., 2008): an HxxHHH motif in an environment rich in arginines (R) and lysines (K) is essential for 3-ketoacyl-CoA synthase activity for saturated or monounsaturated fatty acid elongation; a LYF motif, also present in sequences of yeast elongases of the Fen1p superfamily, which accepts fatty acids with an acyl chain of 18 to 24 carbon atoms as substrates; a retention signal in the endoplasmic reticulum associated with a K-rich motif in the C-terminal part (Jackson et al., 1990); seven transmembrane domains (PM) predicted with the TMHMM Server v. 2.0 (http://www.cbs.dtu.dk/services/TMHMM).

FIG. 5 shows a sequence alignment of *Nannochloropsis gaditana* elongase Naga_100083g23 with a *Phaeodactylum* Δ0-elongase (SEQ ID NO 7) using the Smith-Waterman method with Blossum 62 comparison matrix (Rice et al., 2000): Matrix: EBLOSUM62, "Gap_penalty": 10.0, "Extend_penalty": 0.5, Length: 287, Identity: 123/237 (51.9%), Similarity: 161/237 (67.9%), Gaps: 2/237 (0.8%), Score: 690.5.

FIG. 6 shows a sequence alignment of *Nannochloropsis gaditana* elongase Naga_100083g23 with a *Thalassiosira* Δ0-elongase (SEQ ID NO 8) using the Smith-Waterman method with Blossum 62 comparison matrix (Rice et al., 2000): Matrix: EBLOSUM62, "Gap_penalty": 10.0, "Extend_penalty": 0.5, Length: 237, Identity: 135/287 (47.0%), Similarity: 178/287 (62.0%), Gaps: 16/287 (5.6%), Score: 713.5.

DETAILED DESCRIPTION OF THE INVENTION

Figure 1:
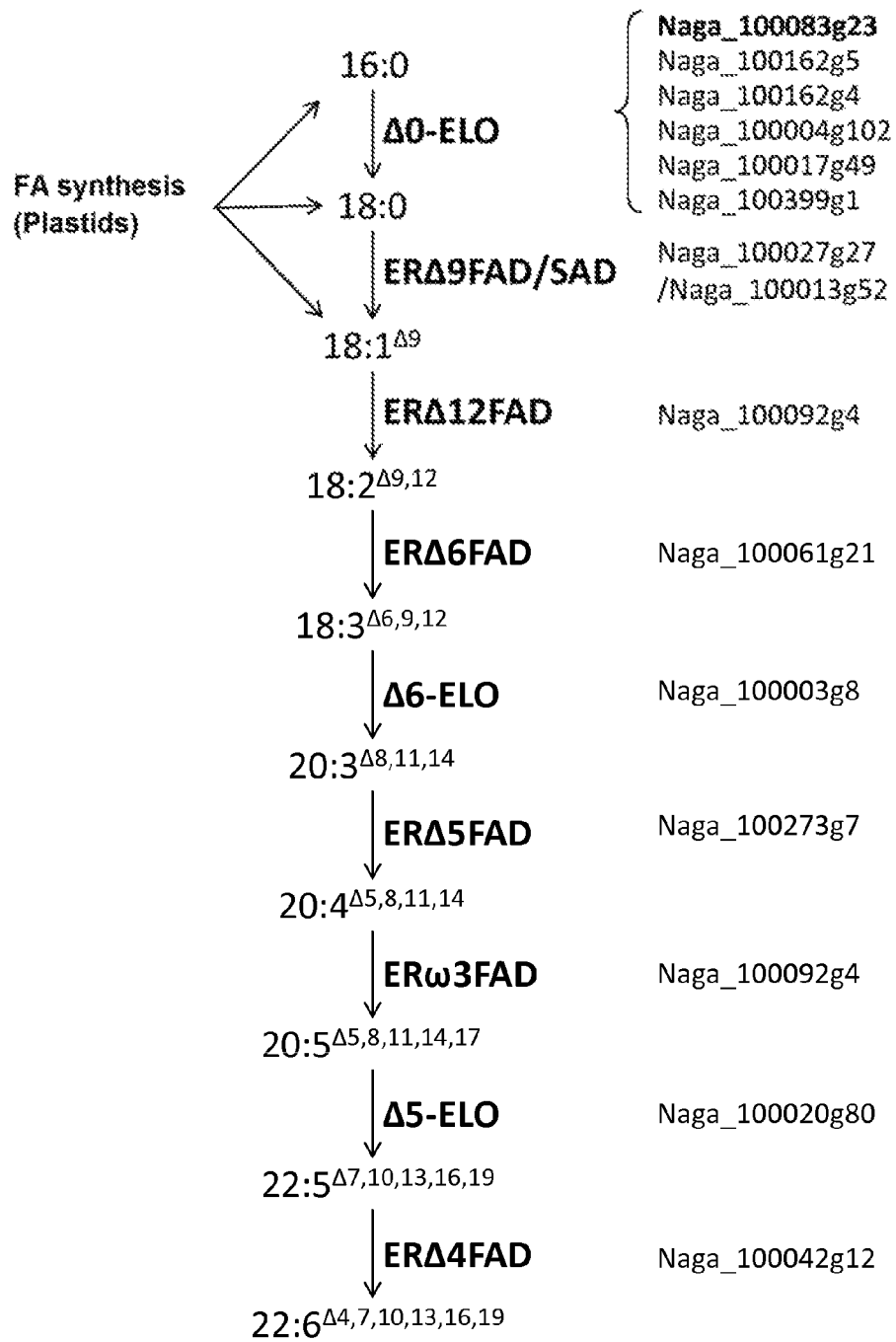
FIG. 1 shows the reconstructed biosynthesis pathway of very-long-chain polyunsaturated fatty acids in *Nannochloropsis gaditana*. Fatty acid synthesis in the chloroplast can generate 16:0 (palmitic acid), 18:0 (stearic acid) and 18:1 (oleic acid) precursors which are exported to the cytosol. Desaturation of 18:0 into 18:1 can occur either by a chloroplast stearoyl-ACP Δ9-desaturase (SAD) or an endoplasmic reticulum Δ9-desaturase (ERΔ9FAD). Eight candidate genes encoding elongases and six genes encoding desaturases were identified in the *N. gaditana* genome. Elongases identified as capable of transforming a 16:0 saturated substrate are referred to as Δ0-ELO. Elongases identified as capable of transforming an unsaturated substrate with a double bond at position Δ6 (18:3) are referred to as Δ6-ELO. Those identified as capable of transforming an unsaturated substrate with a double bond at position Δ5 (20:5) are referred to as Δ5-ELO.
Figure 3:
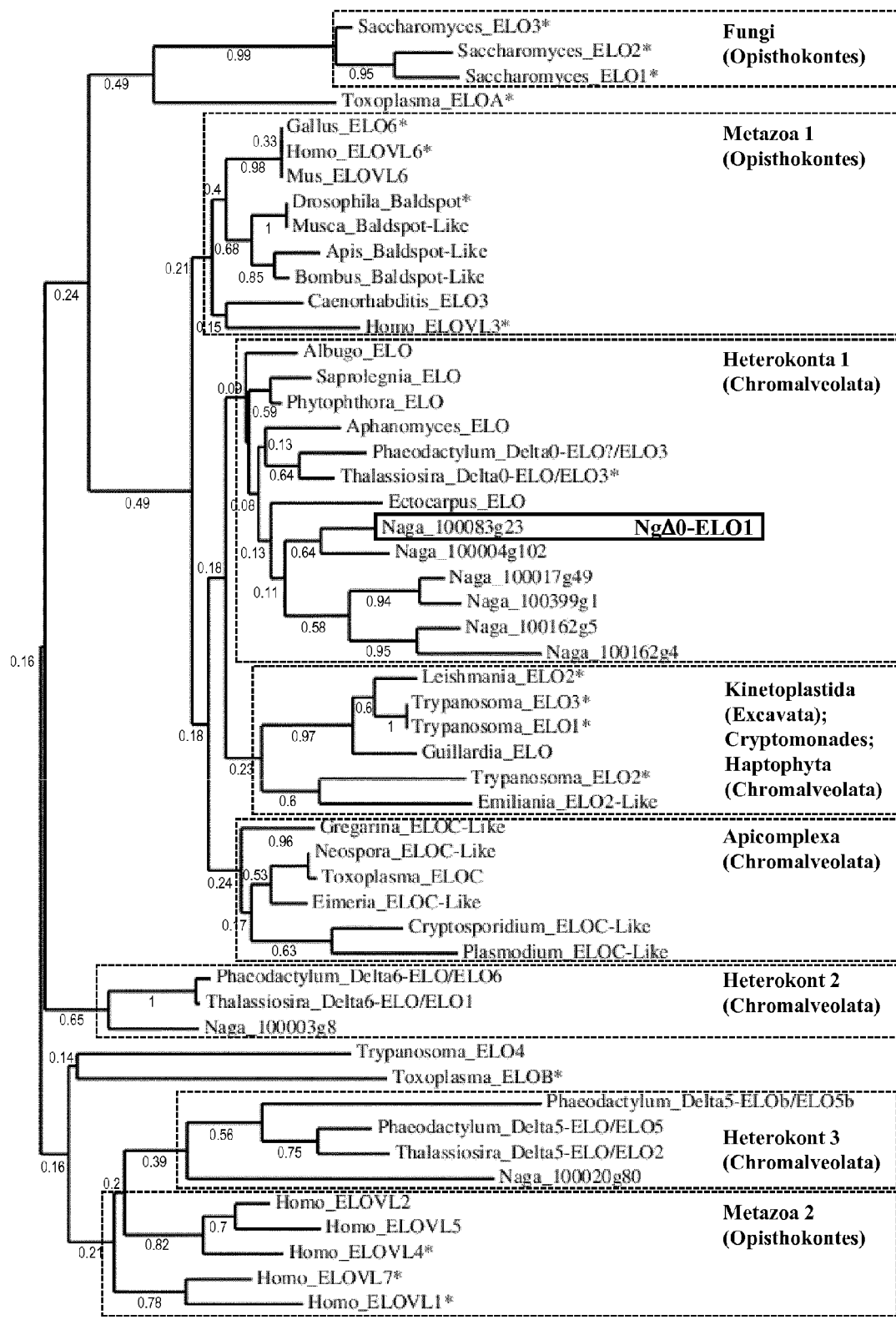
FIG. 3 shows the phylogenetic tree of putative fatty acid elongases or those identified in the literature as such by groups representative of eukaryotes. Selected sequences cover the biodiversity of eukaryotes, including Opisthokonts, e.g. Fungi (*Saccharomyces*) and Metazoa (*Drosophila, Musca, Apis, Bombus, Caenorhabditis, Homo, Mus, Gallus*), Heterokonts (*Phaeodactylum, Thalassiosira, Ectocarpus, Phytophthora, Albugo, Saprolegnia, Aphanomyces*), Apicomplexa (*Toxoplasma, Neospora, Eimeria, Cryptosporidium, Plasmodium, Gregarina*), Haptophytes (Emiliania), Cryptomonads (Guillardia) and Kinetoplastida (*Trypanosoma, Leishmania*). The amino acid sequences were aligned using the MUSCLE program and the phylogenetic tree was constructed using the Neighbour-Joining method. A star indicates sequences characterized or proposed as elongases in the literature (Cook and Hildebrand, 2015; Jung et al., 2007; Kihara, 2012; Lee et al., 2006; Ramakrishnan et al., 2012; Tehlivets et al., 2007).

The present invention concerns genetically modified microalgae in which the Δ0-elongase (Δ0-ELO) activity is inhibited. Δ0-Elongases are those that accept a saturated fatty acid as substrate, particularly palmitic acid. The microalgae according to the invention produce more TAG than corresponding microalgae whose elongase activity is not inhibited (FIG. 8), while having growth and biomass production properties that are not substantially affected relative to the corresponding unmodified strain (FIG. 9). The microalgae according to the invention are genetically modified so that the Δ0-ELO activity is inhibited, more particularly the Δ0-ELO activity associated with the production of monogalactosyldiacylglycerol (MGDG). Indeed, the inventors were able to conclude that despite the inhibition of Δ0-ELO activity associated with MGDG production, the genetically modified strains continued to produce it, allowing unaltered growth and biomass production relative to the same unmodified strain.

According to the invention, "genetically modified" means any modification of the genome of the microalgae obtained by human intervention or under human control consisting in introducing a heterologous nucleic acid sequence into the genome of the microalgae. The result of this modification is to enrich the genome of the genetically modified microalga with the addition of new sequences and/or to reduce it by removing fragments of native sequences.

"Heterologous nucleic acid sequence" means any synthetic sequence prepared by, or under the control of, a human being, notably by copying a natural gene by any known replication technique such as PCR, by assembling fragments of natural genes, with or without introduction of mutations. It may be a sequence encoding a gene of interest with or without sequences for regulating its expression in a host organism, or synthetic fragments with no function other than to introduce into a target gene a mutation intended to inhibit its expression (KO). The heterologous nucleic acid sequence advantageously includes nucleic acid fragments for targeting its introduction into a target gene by any known technique of homologous recombination or targeting of a DNA sequence.

Techniques for transforming microalgae are well known to the skilled person. The same is true for gene targeting techniques. In particular, mention may be made of (Kilian et al., 2011) or application WO 2014/207043.

The invention is particularly suitable for microalgae containing photosynthetic organelles such as chloroplasts. The effect obtained was more particularly identified for such microalgae that produce the 16:0 precursor (palmitoyl-CoA) in chloroplasts.

These microalgae are well known to the skilled person. Particular mention may be made of the microalgae of the genera *Crypthecodinium, Chlorella, Cyclotella, Euglena, Haematococcus, Isochrysis, Monodus, Nanochloris, Nannochloropsis, Nitzschia, Odontella, Phaeodactylum, Scenedesmus, Tetraselmis*, and *Thalassiosira*.

The inventors were able to demonstrate that the Δ0-ELO activity could be multigenic in microalgae. The invention is more particularly suitable for inhibiting the Δ0-ELO activity in microalgae for which the Δ0-ELO activity is multigenic, more particularly when only the Δ0-ELO activity associated with MGDG production is inhibited.

The invention is more particularly suitable for microalgae whose inhibited Δ0-ELO activity is encoded by a gene encoding a protein of SEQ ID NO 1 or a homologous sequence comprising at least 40% identity, preferably at least 45% identity with SEQ ID NO 1 and comprises an HxxHH motif in an R- and K-rich environment, and a K-rich motif in its C-terminal part.

These structural elements are common to elongases and were identified in SEQ ID NO 1 encoded by the Naga_100083g23 gene (FIG. 4) and are found in the other *Nannochioropsis gaditana* Δ0-ELO sequences (FIG. 2) and in the *Phaeodactylum* (FIG. 5) and *Thalassiosira* (FIG. 6) sequences.

With these structural elements common to elongases, the homologous sequences have at least 100 amino acids identical to those of SEQ ID NO 1, preferably at least 120 identical amino acids.

The skilled person will be able to identify other sequences homologous to SEQ ID NO 1 from known sequences or those obtained from the genome of microalgae and by conventional single or multiple alignment methods such as the Clustal methods (Sievers F. et al., 2011) or based on the Smith-Waterman method with Blossum 62 comparison matrix (Rice et al., 2000).

Advantageously, the microalgae according to the invention are selected from the microalgae of the genera *Phaeodactylum*, *Thalassiosira* and *Nannochloropsis* identified to have genes encoding sequences homologous to SEQ ID NO 1, notably the proteins represented by SEQ ID NO 7 and SEQ ID NO 8.

According to a more preferential embodiment of the invention, the microalgae are of the species *Nannochloropsis gaditana* which has a gene encoding the elongase represented by SEQ ID NO 1.

The skilled person knows several ways to inhibit Δ0-ELO activity. For example, the microorganism can be modified to promote the production of a substrate that binds to the enzyme in competition with the 16:0 fatty acid. The microorganism can also be modified to express a nucleic acid that will inhibit translation of the gene encoding Δ0-ELO. The microorganism can also be modified to express a nucleic acid that will inhibit transcription of the gene encoding Δ0-ELO. According to a preferred embodiment of the invention, the microalgae are transformed by introducing a mutation into the gene encoding Δ0-ELO. This mutation has the effect of inhibiting expression of the gene (KO). The mutation may consist in adding a nucleic acid or a nucleic acid fragment so as to insert a "stop" codon in the coding part of the gene. The mutation may also consist in removing nucleic acid fragments in the gene, in the promoter regulatory sequence and/or in the coding sequence. The mutation may consist of a complete removal of the targeted gene from the genome of the genetically modified microalgae.

Methods for transforming microalgae to introduce a KO of a target gene are known to the skilled person, who will be able to adapt them to target the gene encoding Δ0-ELO. Particular mention may be made of (Kilian et al., 2011) or application WO 2014/207043.

According to a preferred embodiment of the invention, the genetically modified microalgae are *Nannochloropsis gaditana* modified by KO of the Naga_100083g23 gene encoding the Δ0-ELO1 of SEQ ID NO 1.

The invention also concerns the production of a biomass enriched in triacylglycerols (TAGs), comprising culturing genetically modified microalgae according to the invention in a culture medium suitable for promoting their growth and cell multiplication.

Microalgae culture methods are well known to the skilled person, whether in autotrophic, heterotrophic or mixotrophic mode. According to a preferred embodiment of the invention, the culture is carried out with provision of light in autotrophic or mixotrophic mode. Particular mention may be made of the culture methods described in applications WO 2012/035262 and WO 2015/004403. Of course, the skilled person will be able to adapt the culture conditions, notably the composition of the medium, the conditions for adding nutrients during the culture, the temperature and oxygenation cycles, and the lighting conditions, in order to promote biomass production.

The invention also concerns a process for producing triacylglycerols (TAGs), comprising obtaining a TAG-enriched biomass according to the invention and isolating TAGs from the biomass. Methods for isolating TAGs from biomass are well known to the skilled person. Particular mention may be made of processes comprising steps of recovering biomass from the culture medium, for example by filtration or centrifugation, then drying said biomass before extracting the fats, including TAGs, by pressing. Particular mention may be made of the methods described by Bligh, E. G. and Dyer, W. J. (1959) or in application WO 1997/037032.

The isolated TAGs may also be purified by known purification methods such as liquid/liquid extraction or distillation under reduced pressure.

The invention also concerns a TAG-enriched biomass obtained by the process according to the invention.

According to the invention, "biomass" advantageously means a set of microalgal cells produced by their culture, which may or may not have retained their physical integrity. It is therefore understood that said biomass may include a quantity of degraded microalgal cells ranging from 0% to 100%. "Degraded" means that the physical integrity of said microalgal cells may have been altered, such as for example lysed microalgae, resulting for example from a homogenization process. Once produced, this biomass may be raw, in its culture medium or isolated therefrom, optionally dried, optionally degraded.

Finally, the invention concerns the TAGs obtained by the process according to the invention, in particular a TAG-enriched oil which has not been substantially modified relative to the oil extracted from the biomass according to the invention.

EXAMPLES

Materials and Methods

*N. Gaditana* Strains and Culture Conditions

*Nannochloropsis gaditana* CCMP526 wild-type strains (NgWT) and mutants are maintained in an f/2 medium (Guillard and Ryther, 1962) containing modified sea salts (NaCl, 21.194 g·L$^{-1}$; Na$_2$SO$_4$, 3.55 g·L$^{-1}$; KCl, 0.599 g·L$^{-1}$; NaHCO$_3$, 0.174 g·L$^{-1}$; KBr, 0.0863 g·L$^{-1}$; H$_3$BO$_3$, 0.023 g·L$^{-1}$; NaF, 0.0028 g·L$^{-1}$; MgCl$_2$.6H$_2$O, 9.592 g·L$^{-1}$; CaCl$_2$.2H$_2$O, 1.344 g·L$^{-1}$; and SrCl$_2$.6H$_2$O, 0.0218 g·L$^{-1}$; NaNO$_3$, 46.67 mg·L$^{-1}$ and NaH$_2$PO$_4$, 3.094 mg·L$^{-1}$) under gentle agitation at 20° C. with either an alternating 12 h/12 h night/day light cycle or continuous lighting under white light with a photon flux of 30 µmol·m$^{-2}$ s$^{-1}$. Cultures in Erlenmeyer flasks (50-100 mL) or on 24-well plates (2 mL) are inoculated with a density of $20^6$ cells·mL$^{-1}$.

The cells are stored at −80° C. in DMSO or may be maintained on 1.5% agar plates supplemented with f/2 medium and subcultured monthly.

Cell densities are measured by absorbance at 750 nm of 300 µL culture aliquots (TECAN Infinite M1000Pro). All measurements are made on at least three biological samples, each representing an individual culture of the same strain.

Cloning of the Naga_100083g23 Gene (Δ0-ELO1) KO Cassette and Transformation of *N. Gaditana* CCMP526

The transformation vector comprises a p35S-LoxP cassette, a zeocin resistance gene (ZEO, CDS 3078-3448) under the control of the ubiquitin promoter, and the *Phaeodactylum tricornutum* FcpA terminator. Two flanking regions containing the recognition sites of the restriction enzymes specific to the target gene to allow KO by insertion into the genomic DNA by homologous recombination after transformation (Kilian et al., 2011). The flanking sequences of the Naga_100083g23 gene (Δ0-ELO1) are amplified by PCR using the oligonucleotide pairs 5'-gttgggaataatgcgggacc-3' (SEQ ID NO 9) and 5'-ccgctttggtttcacagtca-3' (SEQ ID NO 10) for the terminal flank and 5'-acgatgggtatgttgcttgc-3' (SEQ ID NO 11) and 5'-tgtacagggcggatttcact-3' (SEQ ID NO 12) for the upstream flank.

*Nannochloropsis gaditana* CCMP526 wild-type strains are transformed with the transformation vector according to the method described by Killian et al. with the following modifications: $10^8$ NgWT cells are harvested during the exponential growth phase at a concentration of $30^6$ cells·mL$^{-1}$, washed twice with 375 mM D-sorbitol then resuspended in 100 µL final volume. The recombination cassette is digested from the vector and 1 µg of the digestion product is mixed with the suspension. After 15 minutes of incubation on ice, the cells are electroporated (NEPA21 Type II, Sonidel Ltd; BioRad MicroPulser). The transformation mix is transferred to 5 mL of f/2 medium and incubated for 16 hours under continuous light irradiation. Cells are then plated on 1.5% f/2 agar plates containing 7 µg·ml$^{-1}$ zeocin. Colonies are obtained after 3 to 4 weeks of incubation under continuous light.

Genotyping of Naga_100083g23 KO Mutants (NgΔ0-elo1 KO)

Genotyping of Naga_100083g23 KO mutants was performed by PCR by assessing the presence of the zeocin resistance gene flanking sequences and the absence of the Naga_100083g23 gene with the following oligonucleotide pairs: 5'-gaggaatgtgtgtggttggg-3' (SEQ ID NO 13) for the zeocin resistance gene promoter and 5'-gccgtattgttggagtg-gac-3' (SEQ ID NO 14) for the terminator sequence; 5'-ga-cacttctctgcctttgcc-3' (SEQ ID NO 15) and 5'-atggtggtacca-gtggagga-3' (SEQ ID NO 16) for the Naga_100083g23 gene.

The number of cassettes inserted into the *N. gaditana* genome in three independent clones was quantified by qPCR on DNA extracted using the chloroform-phenol method (Pacific Biosciences of California, Inc, 2012; Cao et al., 2012) and using the following oligonucleotides: Naga_100083g23F 5'-gtgggcaccaaggttatgga-3' (SEQ ID NO 17); Naga_100083g23R 5'-gaaggaggtgtggtacggtg-3' (SEQ ID NO 18); papF 5'-aagtggtacctttgctccgt-3' (SEQ ID NO 19); papR 5'-aaggtagccgagtagccaaa-3' (SEQ ID NO 20); tubF 5'-ttgagcataccgacgtgact-3' (SEQ ID NO 21); tubR 5'-gcgatgagcctgttcagatt-3' (SEQ ID NO 22); zeoF 5'-tgtgc-caaaatcatacagcagg-3' (SEQ ID NO 23); zeoR 5'-cgaagtcgtc-ctccacgaag-3' (SEQ ID NO 24).

Lipid Extraction and Analysis

Lipid extraction and analysis were performed according to the methods described by Simionato et al. (2013). Mass spectrometric analysis was performed by comparison with standards described by Abida et al. (2015).

Results

Figure 7B:
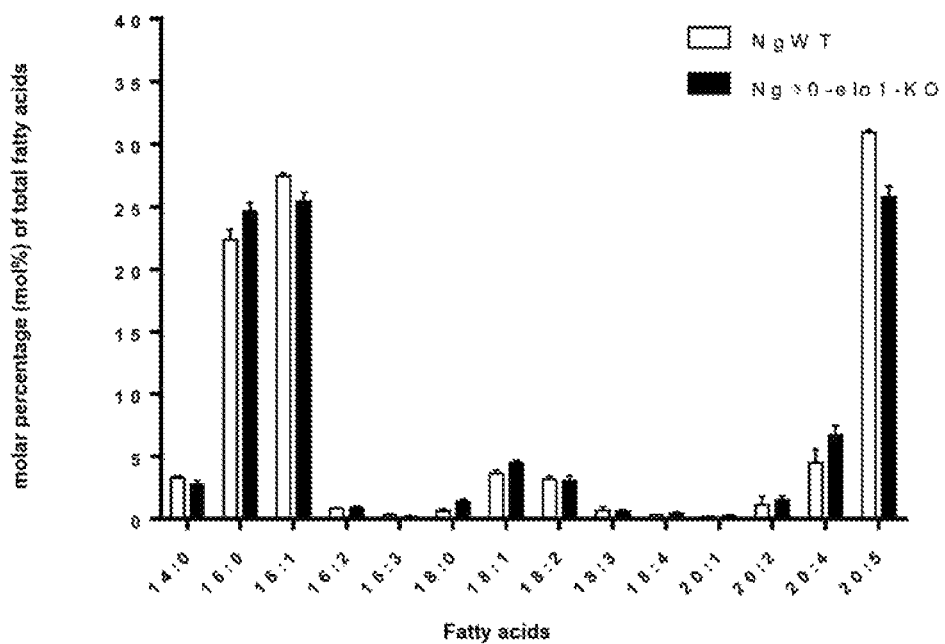
FIG. 7 shows the overall fatty acid analysis of *Nannochloropsis gaditana* wild-type (WT) lines and lines transformed by KO of the NgΔ0-ELO1 gene (NgΔ0-ELO1-KO).
Figure 8:
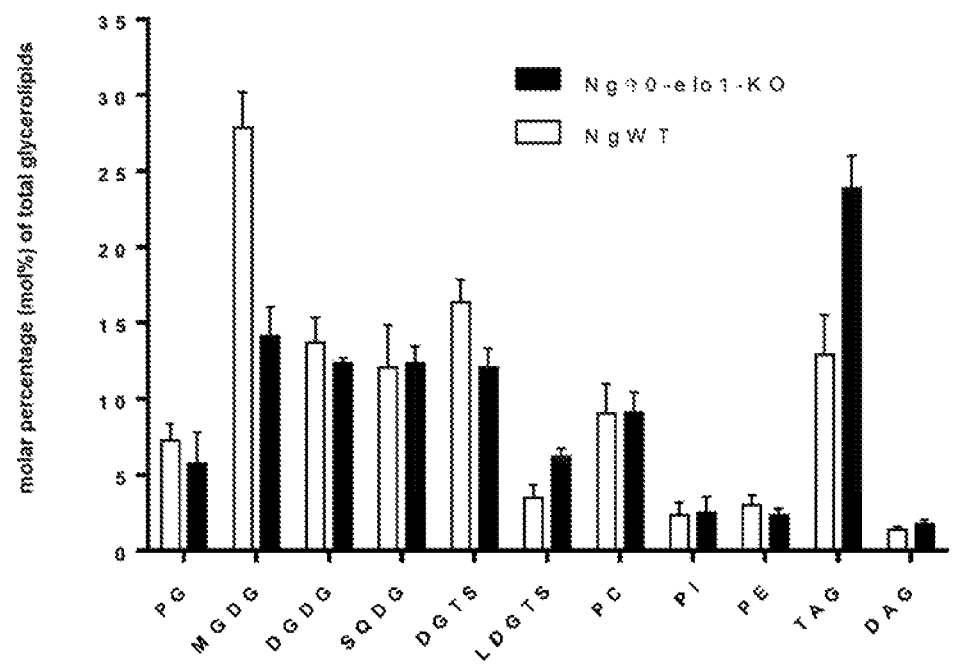
FIG. 8 shows the glycerolipid profile of *Nannochloropsis gaditana* wild-type (WT) lines and lines transformed by KO of the NgΔ0-ELO1 gene (NgΔ0-ELO1-KO): phosphatidylglycerol (PG), monogalactosyldiacylglycerol (MGDG), digalactosyldiacylglycerol (DGDG), sulphoquinovosyldiacylglycerol (SQDG), diacylglyceryltrimethylhomoserine (DGTS), lyso-DGTS (LDGTS), (PC), phosphatidylinositol (PI), phosphatidylethanolamine (PE), triacylglycerol (TAG) and diacylglycerol (DAG).
Figure 9A:
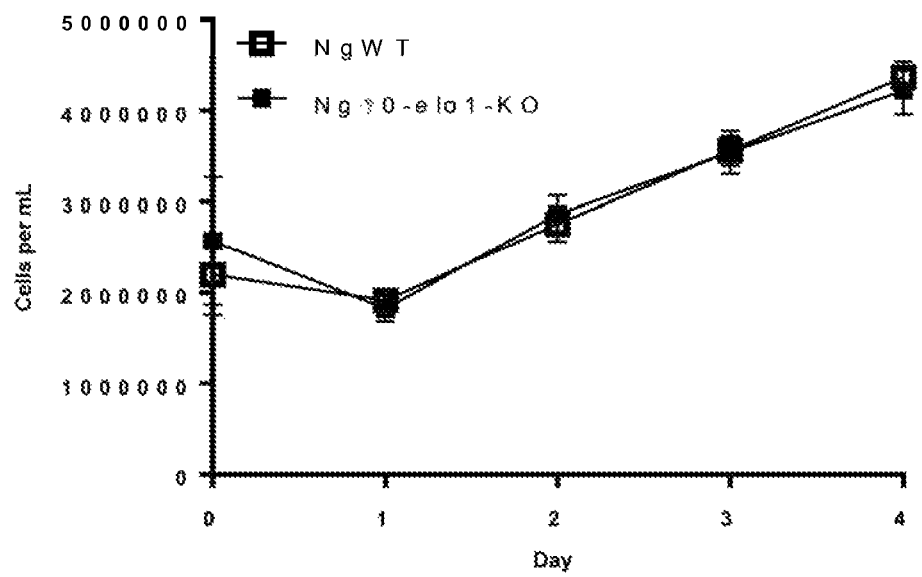
FIG. 9 shows the growth and biomass obtained by culturing *Nannochloropsis gaditana* wild-type (WT) lines and lines transformed by KO of the NgΔ0-ELO1 gene (NgΔ0-ELO1-KO).
Figure 9B:
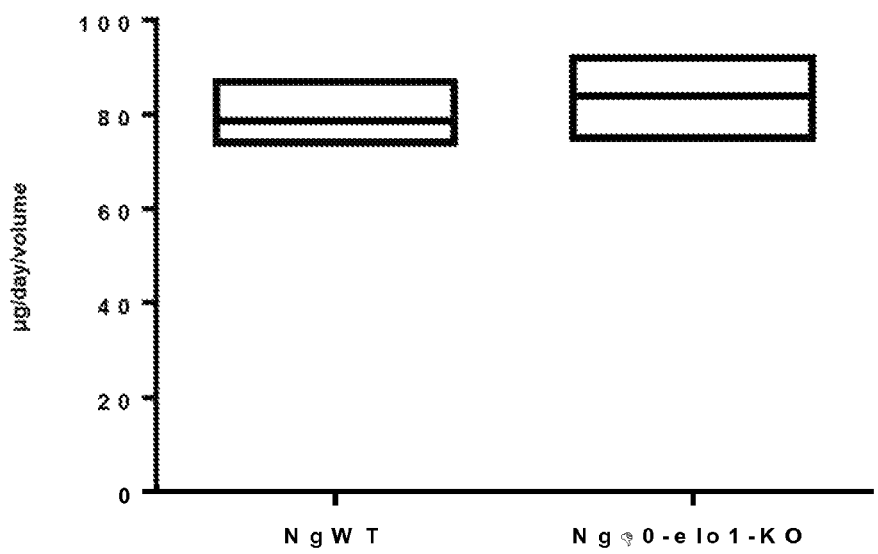

The results obtained are shown in FIGS. 7 to 9. No statistically significant difference is observed in the amounts of lipids produced between the wild-type (WT) strains and the NgΔ0-elo1 KO mutants (FIG. 7.A). However, a change in the type of fatty acids produced is observed (FIG. 7.B), with an 8% decrease in the amount of eicosapentaenoic acid, or EPA (20:5), produced.

When the different glycerolipids produced are compared (FIG. 8), a marked difference between the WT strains and the NgΔ0-elo1 KO mutants is observed, with a decrease in MGDG production (−43.8%) and an increase in TAG production (+71%) in the mutants.

Finally, when growth curves (FIG. 9A) and biomass production (FIG. 9B) are compared, it is seen that inhibition of Naga_100083g23 gene expression in the mutants does not alter these properties.

Glycerolipid analyses show a relationship between the KO of the Naga_100083g23 gene encoding Δ0-ELO1, a decrease in EPA synthesis, a decrease in MGDG synthesis, and a concomitant increase in TAG synthesis. The biomass produced being the same, an increase in TAG production by a factor of 1.7 to 2 is obtained.

REFERENCES

Patents and Patent Applications

U.S. Pat. No. 8,809,046
WO 96/21022
WO 1997/037032
WO 2012/035262
WO 2014/207043
WO 2015/004403

PUBLICATIONS

Abida H, Dolch L J, Mei C, Villanova V, Conte M, Block M A, Finazzi G, Bastien O, Tirichine L, Bowler C, Rebeille F, Petroutsos D, Jouhet J, Marechal E (2015) Membrane glycerolipid remodeling triggered by nitrogen and phosphorus starvation in *Phaeodactylum tricornutum*. Plant Physiol 167: 118-136.

Bligh, E. G. et Dyer, W. J. (1959); A rapid method of total lipid extraction and purification, Can. J. Biochem. Physiol., 37:911-917.

Cook O, Hildebrand M (2015) Enhancing LCPUFA production in *Thalassiosira pseudonana* by overexpressing the endogenous fatty acid elongase genes. J Appl Phycol 1-9.

Cao S, Zhang X, Ye N, Fan X, Mou S, Xu D, Liang C, Wang Y, Wang W (2012) Evaluation of putative internal reference genes for gene expression normalization in *Nannochloropsis* sp. by quantitative real-time RT-PCR. Biochem Biophys Res Commun 424: 118-123.

Denic V, Weissman J S (2007) A molecular caliper mechanism for determining very longchain fatty acid length. Cell 130: 663-677.

Guillard R R, Ryther J H (1962) Studies of marine planktonic diatoms. I. *Cyclotella nana* Hustedt, and *Detonula confervacea* (cleve) Gran. Canadian journal of microbiology 8: 229-239.

Hashimoto K, Yoshizawa A C, Okuda S, Kuma K, Goto S, Kanehisa M (2008) The repertoire of desaturases and elongases reveals fatty acid variations in 56 eukaryotic genomes. J Lipid Res 49: 183-191.

Jackson M R, Nilsson T, Peterson P A (1990) Identification of a consensus motif for retention of transmembrane proteins in the endoplasmic reticulum. EMBO J 9: 3153-3162.

Jung A, Hollmann M, Schafer M A (2007) The fatty acid elongase NOA is necessary for viability and has a somatic role in *Drosophila* sperm development. J Cell Sci 120: 2924-2934.

Kihara A (2012) Very longchain fatty acids: elongation, physiology and related disorders. J Biochem 152: 387-395.

Kilian O, Benemann C S, Niyogi K K, Vick B (2011) Highefficiency homologous recombination in the oilproducing alga *Nannochloropsis* sp. Proc Natl Acad Sci USA 108: 21265-21269.

Lee S H, Stephens J L, Paul K S, Englund P T (2006) Fatty acid synthesis by elongases in trypanosomes. Cell 126: 691-699.

Ramakrishnan S, Docampo M D, Macrae J I, Pujol F M, Brooks C F, van Dooren G G, Hiltunen J K, Kastaniotis A J, McConville M J, Striepen B (2012) Apicoplast and endoplasmic reticulum cooperate in fatty acid biosynthesis in apicomplexan parasite *Toxoplasma gondii*. J Biol Chem 287: 4957-4971.

Sievers F, Wilm A, Dineen D, Gibson T J, Karplus K, Li W, Lopez R, McWilliam H, Remmert M, Söding J, Thompson J D, Higgins D G (2011) Fast, scalable generation of highquality protein multiple sequence alignments using Clustal Omega. Molecular Systems Biology, 7:539

Simionato D, Block M A, La Rocca N, Jouhet J, Marechal E, Finazzi G, Morosinotto T (2013) The response of *Nannochloropsis gaditana* to nitrogen starvation includes de novo biosynthesis of triacylglycerols, a decrease of chloroplast galactolipids, and reorganization of the photosynthetic apparatus. Eukaryot Cell 12: 665-676.

Rice P., Longden I., Bleasby A. (2000) EMBOSS: The European Molecular Biology Open Software Suite. Trends in Genetics, 16(6):276-277

Tehlivets O, Scheuringer K, Kohlwein S D (2007) Fatty acid synthesis and elongation in yeast. Biochim Biophys Acta 1771: 255-270.

The invention claimed is:

1. A genetically modified microalgae wherein a acne encoding Δ0-elongase (Δ0-ELO) activity is inhibited by knockout (KO), and wherein the Δ0-elongase (Δ0-ELO) consists of the amino acid sequence as set forth in SEQ ID NO 1 or a homologous sequence comprising at least 45% identity with SEQ ID NO 1 and having at least 120 amino acids identical to those of SEQ ID NO 1 with the amino acid motif HxxHHH present in an R- and K-rich environment and a K-rich motif in its C-terminal part.

2. The genetically modified microalga according to claim 1, wherein the microalga is selected from microalgae containing photosynthetic organelles.

3. The genetically modified microalga according to claim 2, wherein the microalga containing photosynthetic organelles is selected from the microalgae of the genera *Crypthecodinium, Chlorella, Cyclotella, Euglena, Haematococcus, Isochrysis, Monodus, Nanochloris, Nannochloropsis, Nitzschia, Odontella, Phaoedactylum, Scenedesmus, Tetraselmis,* and *Thalassiosira*.

4. The genetically modified microalga according to claim 1, wherein the microalga is selected from the microalgae of the genera *Phaoedactylum, Thalassiorisa* and *Nannochloropsis*.

5. The genetically modified microalga according to claim 1, wherein the microalga is a *Nannochloropsis gaditana* modified by KO of the Naga_100083g23 gene encoding the Δ0-ELO1 of SEQ ID NO 1.

6. A process for producing a biomass enriched in triacylglycerols (TAGs) comprising: culturing the genetically modified microalgae according to claim 1 in a culture medium suitable for promoting the growth and multiplication of microalgal cells.

7. A process for producing triacylglycerols (TAGs) comprising: obtaining the TAG-enriched biomass according to claim 6 and isolating TAGs from biomass.

8. Biomass comprising the genetically modified microalgae according to claim 1.

* * * * *

UNITED STATES PATENT AND TRADEMARK OFFICE
CERTIFICATE OF CORRECTION

PATENT NO. : 10,724,011 B2
APPLICATION NO. : 16/308226
DATED : July 28, 2020
INVENTOR(S) : Lina Juana Dolch et al.

Page 1 of 1

It is certified that error appears in the above-identified patent and that said Letters Patent is hereby corrected as shown below:

In the Claims

Claim 1, Column 29, Line 1, "A genetically modified microalgae wherein a acne..." should read --A genetically modified microalgae wherein a gene--.

Signed and Sealed this
Twenty-fourth Day of November, 2020

Andrei Iancu
*Director of the United States Patent and Trademark Office*